US012605485B2

(12) United States Patent
Drake

(10) Patent No.: US 12,605,485 B2
(45) Date of Patent: *Apr. 21, 2026

(54) NANOPARTICLES TO PROMOTE WOUND HEALING AND ANTIMICROBIAL INFECTION CONTROL

(71) Applicant: KISMET TECHNOLOGIES LLC, Winter Park, FL (US)

(72) Inventor: Christina H. Drake, Winter Park, FL (US)

(73) Assignee: Kismet Technologies Inc., Orlando, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/973,640

(22) Filed: Oct. 26, 2022

(65) Prior Publication Data

US 2023/0137084 A1     May 4, 2023

Related U.S. Application Data

(60) Provisional application No. 63/272,930, filed on Oct. 28, 2021.

(51) Int. Cl.

| | |
|---|---|
| *A61L 26/00* | (2006.01) |
| *A61K 9/14* | (2006.01) |
| *A61K 33/00* | (2006.01) |
| *A61K 33/24* | (2019.01) |
| *A61K 33/242* | (2019.01) |
| *A61K 33/243* | (2019.01) |
| *A61K 33/26* | (2006.01) |
| *A61K 33/30* | (2006.01) |
| *A61K 33/34* | (2006.01) |
| *A61K 33/38* | (2006.01) |
| *A61K 38/19* | (2006.01) |
| *A61K 47/10* | (2017.01) |
| *A61K 47/34* | (2017.01) |
| *A61K 47/36* | (2006.01) |
| *A61K 47/42* | (2017.01) |
| *A61K 48/00* | (2006.01) |
| *A61P 27/02* | (2006.01) |

(52) U.S. Cl.
CPC ............ *A61L 26/0066* (2013.01); *A61K 9/14* (2013.01); *A61K 33/00* (2013.01); *A61K 33/24* (2013.01); *A61K 33/242* (2019.01); *A61K 33/243* (2019.01); *A61K 33/26* (2013.01); *A61K 33/30* (2013.01); *A61K 33/34* (2013.01); *A61K 33/38* (2013.01); *A61K 38/19* (2013.01); *A61K 47/10* (2013.01); *A61K 47/34* (2013.01); *A61K 47/36* (2013.01); *A61K 47/42* (2013.01); *A61L 26/0095* (2013.01); *A61P 27/02* (2018.01); *A61K 48/00* (2013.01); *A61L 2300/104* (2013.01); *A61L 2300/402* (2013.01); *A61L 2300/404* (2013.01); *A61L 2300/41* (2013.01); *A61L 2400/12* (2013.01)

(58) Field of Classification Search
CPC .......... A61K 9/14; A61K 33/24; A61K 33/00; A61K 33/38
See application file for complete search history.

(56) References Cited

U.S. PATENT DOCUMENTS

| | | | |
|---|---|---|---|
| 4,826,893 A | 5/1989 | Yamazaki et al. | |
| 4,866,042 A | 9/1989 | Neuwelt | |
| 5,223,425 A | 6/1993 | Flier et al. | |
| 5,290,552 A | 3/1994 | Sierra et al. | |
| 5,464,764 A | 11/1995 | Capecchi et al. | |
| 5,487,992 A | 1/1996 | Capecchi et al. | |
| 7,638,484 B2 | 12/2009 | Braiman-Wilksman et al. | |
| 8,400,408 B2 | 3/2013 | Hotelling et al. | |
| 8,507,431 B2 | 8/2013 | Braiman-Wilksman et al. | |
| 10,155,361 B2 | 12/2018 | Bookbinder et al. | |
| 10,289,225 B2 | 5/2019 | Jin et al. | |
| 10,642,426 B2 | 5/2020 | Hwang et al. | |
| 10,925,773 B2 | 2/2021 | Riesinger | |
| 2006/0155041 A1* | 7/2006 | Suzuki ................... A61L 27/14 | 524/495 |

(Continued)

FOREIGN PATENT DOCUMENTS

| | | |
|---|---|---|
| CA | 2644315 | 10/2007 |
| CN | 101138342 | 5/2011 |

(Continued)

OTHER PUBLICATIONS

Sadidi et al (Molecules, Oct. 6, 2020 (online), vol. 25, pp. 1-25) (Year: 2020).*
Neal et al (ACS Nano, Aug. 2021, vol. 15, pp. 14544-14556) (Year: 2021).*
Hanafy et al (Molecules, Jan. 2020, vol. 25, pp. 1-16) (Year: 2020).*
Maleki et al (Inorganic Chemistry Communications, Jun. 2021, vol. 131, pp. 1-9). (Year: 2021).*
Mitchell et al (Nature Communications, Nov. 2017, vol. 8, pp. 1-7) (Year: 2017).*
International Search Report, Feb. 14, 2023.

(Continued)

*Primary Examiner* — Mark V Stevens
(74) *Attorney, Agent, or Firm* — Terry M. Sanks, Esq.; Beusse Sanks, PLLC

(57) ABSTRACT

A wound healing composition is provided that includes a tissue adhesive or epithelial tissue healing agent and metal-modified cerium oxide nanoparticles (mCNPs). The nCNPs have a predominant 3+ surface charge and are in a range of about 3-35 nanometers (nm) in size and mixed in an amount that is in a range of about 0.01 to 0.1 weight percentage of a mixture having the tissue adhesive or epithelial tissue healing agent and the mCNPs. The metal (m) is a stable metallic metal with antimicrobial properties and non-ionizing. The mCNPs includes AgCNP2. A method is provided that uses the healing composition to treat a wound or epithelial tissue. The composition can be used to treat the skin or eye and/or subcutaneous tissue.

22 Claims, No Drawings

(56)                    References Cited

U.S. PATENT DOCUMENTS

| | | | |
|---|---|---|---|
| 2009/0130157 A1 | 5/2009 | Ylitalo et al. | |
| 2011/0002971 A1 | 1/2011 | Hassler et al. | |
| 2012/0020917 A1* | 1/2012 | Braiman-Wiksman | ..................... A61K 35/28 424/85.2 |
| 2012/0107556 A1 | 5/2012 | Zhang et al. | |
| 2013/0115441 A1 | 5/2013 | Bookbinder et al. | |
| 2013/0195927 A1* | 8/2013 | Sudipta | ................ A61K 33/244 424/617 |
| 2013/0211028 A1 | 8/2013 | Shinike et al. | |
| 2015/0059237 A1* | 3/2015 | Difrancesco | ............ C10L 10/02 44/357 |
| 2016/0158403 A1 | 6/2016 | Watson | |
| 2016/0194503 A1 | 7/2016 | Karl | |
| 2017/0202965 A1 | 7/2017 | Baker | |
| 2017/0232139 A1 | 8/2017 | Brownlee et al. | |
| 2017/0252320 A1 | 9/2017 | Martins-Green et al. | |
| 2018/0028431 A1 | 2/2018 | Chiattello et al. | |
| 2018/0110658 A1 | 4/2018 | Lin | |
| 2018/0339913 A1 | 11/2018 | Seal et al. | |
| 2019/0111424 A1 | 4/2019 | Chou et al. | |
| 2019/0262393 A1 | 8/2019 | Pesavento | |
| 2019/0275195 A1 | 9/2019 | Leibler et al. | |
| 2021/0030656 A1 | 2/2021 | Liechty et al. | |

FOREIGN PATENT DOCUMENTS

| | | |
|---|---|---|
| CN | 102559138 | 11/2012 |
| WO | 2005013885 | 2/2005 |
| WO | 2017011886 | 1/2017 |
| WO | 2021222779 | 11/2021 |

OTHER PUBLICATIONS

Neal, Craig J. et al., "schemMetal-Mediated Nanoscale Cerium Oxide Inactivates Human Coronavirus and Rhinovirus , by Surface Disruption," ACS Nano, 2021, 15(9), 14544-14556. doi: 10.1021/acsnano.1c04142.

Szczesio-Wlodarczyk, A. et al., "An Evaluation of the Properties of Urethane Dimethacrylate-Based Dental Resins," Materials, 2021, 14(11):2727. https://doi.org/10.3390/ma14112727.

Xu, Z. et al., "Advances and Impact of Antioxidant Hydrogel in Chronic Wound Healing," Advanced Healthcare Materials, 2020, 9, 1901502. 10.1002/adhm.201901502.

Woodhouse, Ian et al., "Flexible Microneedle Array Patch for Chronic Wound Oxygenation and Biofilm Eradication," ACS Applied Bio Materials, 2021, 4 (7), 5405-5415. doi: 10.1021/acsabm.1c00087.

Cheng et al., "Developing a New Generation of Antimicrobial and Bioactive Dental Resins," Journal of Dental Research, 2017, vol. 96(8): 855-863, doi: 10.177/0022034517709739.

Shcherbakov et al., "Ce02 Nanoparticles-Containing Polymers for Biomedical Applications: A Review," Mar. 17, 2021, Polymers 2021, 3, 924, www.doi.org/10.3390/polym3060924.

OECD Guideline for the Testing of Chemicals No. 439, "In Vitro Skin Irritation: Reconstructed Human Epidermis Test Method," Jul. 23, 2010, OECD Publishing, Paris, https://doi.org/10.1787/9789264090958-en.

Wan, David, (2015). U.N. Ghs: United Nations Globally Harmonized System of Classification and Labeling of Chemicals. CIRS. https://www.cirs-group.com/en/chemicals/un-ghs-globally-harmonized-system-of-classification-and-labeling-of-chemicals.

OECD (2021), Test No. 439: In Vitro Skin Irritation: Reconstructed Human Epidermis Test Method, OECD Guidelines for the Testing of Chemicals, Section 4, OECD Publishing, Paris, https://doi.org/10.1787/9789264242845-en.

European Commission Joint Research Centre, "Statement on the Scientific Validity of In-Vitro Tests for Skin Irritation Testing," Institute for Health and Consumer Protection In-vitro Toxicology Unit, European Centre for the Validation of Alternative Methods (ECVAM) Joint Research Centre (ESAC), Nov. 5, 2008.

OECD Guidelines for the Testing of Chemicals, Test Guideline No. 492, "Reconstructed Human Cornea-like Epithelium (RhCE) Test Method for Identifying Chemicals Not Requiring Classification and Labelling for Eye Irritation or Serious Eye Damage," Section 4, Jun. 25, 2018.

Gwak, J.H. et al., "Identifying the trends in wound healing patents for successful investment strategies," PLoS One, 2017, 12(3): e0174203. https://doi.org/10.1371/journal.pone.0174203.

GHS: Globally Harmonized System of Classification and Labeling of Chemicals (GHS), 8th revised edition, 2019. United Nations—New York and Geneva.

Meng, Z. et al., "Therapeutic Considerations and Conjugated Polymer-Based Photosensitizers for Photodynamic Therapy," Macromolecular Rapid Communications, 2017, 1700614. doi: 10.1002/marc.201700614.

Bhattacharya, Dipsikha et al., "Accelerated and scarless wound repair by a multicomponent hydrogel through simultaneous activation of multiple pathways," Drug Delivery and Translational Research. Dec. 2019;9(6):1143-1158. doi: 10.1007/s13346-019-00660-z. PMID: 31317345.

Kalaycolu, Z. et al., "Antibacterial Nano Cerium Oxide/Chitosan/Cellulose Acetate Composite Films as Potential Wound Dressing," European Polymer Journal (2020), doi: https://doi.org/10.1016/j.eurpolymj.2020.109777.

* cited by examiner

NANOPARTICLES TO PROMOTE WOUND HEALING AND ANTIMICROBIAL INFECTION CONTROL

CROSS-REFERENCE TO RELATED APPLICATIONS

This application claims priority benefit of U.S. Provisional Application No. 63/272,930, titled "NANOPARTICLES TO PROMOTE WOUND HEALING AND ANTIMICROBIAL INFECTION CONTROL," filed Oct. 28, 2021, incorporated herein by reference in its entirety.

BACKGROUND

Embodiments relate to the field of medical science and, more specifically, the field of medicine to treat wounds using a wound healing composite with metal-modified nanoparticles.

In the United States, approximately 7 million patients struggle with chronic wound healing issues. [See Woodhouse et al., "Flexible Microneedle Array Patch for Chronic Wound Oxygenation and Biofilm Eradication," ACS Appl. Bio Mater. 2021, 4, 5405-5415, Jun. 15, 2021, DOI: 10.1021/acsabm.1c00087.] The chance for infection is high with these types of chronic wounds causing the potential for severe health issues. These wounds easily colonize bacteria either from the person's own skin microbiome, or from other contaminated surfaces, tools, or hands.

Wounds that become infected can lead to further serious health complications for the patient, which can be untreatable except through nontraumatic limb amputation. [See Xu et al., "Advances and Impact of Antioxidant Hydrogel in Chronic Wound Healing," Adv. Healthcare Mater. 2020, pgs. 1-11, DOI: 10.1002/adhm.201901502.] Additionally, chronic wound issues often persist due to an inflammation response from the patient's body, not allowing the wound to transition to a proliferative stage where the wound heals and closes. This leaves chronic wound sufferers vulnerable to infection.

SUMMARY

Embodiments relate wound healing compositions, wound healing articles and methods of use to treat wounds using a wound healing composite with metal-modified nanoparticles.

In an aspect, a wound healing composition is provided that includes a tissue adhesive and metal-modified cerium oxide nanoparticles (mCNPs) having a predominant 3+ surface charge and in a range of about 3-5 nanometers (nm) in size and mixed in an amount that is in a range of about 0.01 to 0.1 weight percentage of a mixture having the tissue adhesive and the mCNPs and m is a non-ionizing metal.

In an aspect, a wound healing composition is provided that includes an epithelial tissue healing agent and metal-modified cerium oxide nanoparticles (mCNPs) having a predominant 3+ surface charge and in a range of about 3-5 nm in size and mixed in an amount that is in a range of about 0.01 to 0.1 weight percentage of a mixture having the epithelial tissue healing agent and the mCNPs and m is a non-ionizing metal.

In an aspect, a method is provided for treating skin tissue of a wound with a wound healing composition that includes an epithelial tissue healing agent and the metal-modified cerium oxide nanoparticles having a predominant 3+ surface charge and the metal being non-ionizing.

In an aspect, a method is provided for treating skin tissue with a wound healing composition that includes a tissue adhesive and the metal-modified cerium oxide nanoparticles.

DETAILED DESCRIPTION

The inventor has surprisingly determined that metal-modified cerium oxide nanoparticles (mCNPs), as described herein, destroy bacteria and viruses that are found in wounds associated with epithelial tissue layers of the skin or eye and/or subcutaneous tissue. The inventor has determined that the metal-modified nanoceria of about 0.01 to 0.1 weight (wt.) % in a wound healing composite for skin-type wounds is non-toxic and non-irritating.

The inventor has surprisingly determined that metal-modified cerium oxide nanoparticles (mCNPs), as described herein, destroy bacteria and viruses that are found in ocular wounds or epithelial tissue of the eye. The inventor has determined that the metal-modified nanoceria of about 0.01 to 0.1 weight (wt.) % in an ocular wound healing composite for wounds of the eye is non-toxic and non-irritating.

The inventor has surprisingly determined that metal-modified cerium-oxide nanoparticles can retain their synthetic enzyme behavior using a synthesis technique described herein. These specialized metal bound cerium-oxide nanoparticles can oxidize viruses and bacteria, which cause infections, but also in the presence of a healthy human cell, change its behavior to anti-oxidizing. This behavior allows for antiseptic or antimicrobial properties coupled to inflammation reduction and improved cell growth not common to antimicrobials. In the case of wound healing of the skin or eyes, this allows for faster and more complete wound healing while also preventing infections from a single nanoparticle source.

The metal-modified cerium-oxide nanoparticles, described herein, possess Super Oxide Dismutase (SOD) activity, common to many bio-safe forms of nanoceria. Unlike other nanoceria, the "switch-over" reactions on the nanoceria surface are made fast and more potent by the small presence of discrete silver on the surface of the nanoceria. This allows for quick and facile change in surface behavior of the nanoceria between creation of oxidizing species that are harmful to viruses and bacteria, and to free radical scavenging behavior (antioxidant behavior) that is beneficial to healthy cells. This allows for targeted control of surface reactions from a single material that is able to assist in decrease of inflammation response and support cell growth while also able to target oxidizing behavior directly to viruses and bacteria. This allows for a single system to be an antiseptic to a wound while promoting closure of the wound.

Both wound healing and antimicrobial activity can simultaneously be improved with introduction of ultraviolet (UV) light to the metal mediated cerium oxide nanoparticles. UV light may be introduced via an external light source or with the wound healing apparatus via an up-conversion material that converts visible light to UV or NIR light to UV. [See Meng et al., "Therapeutic Considerations and Conjugated Polymer-Based Photosensitizers for Photodynamic Therapy," Macromol. Rapid Commun. 2017, 1700614, pgs. 1-15, DOI: 10.1002/marc.201700614.] This process may be assisted by polymer conjugation with a photosensitive polymer, such as Tetra-pyrrole structures, or other polymers such as PEG embedded with an up-conversion molecule. This process allows for faster antiviral and antibacterial deactivation in wound healing applications where the wound being treated has its kinetics slowed by oxygen or water diffusion, where the light activation would assist speeding the kinetics of both antiviral and antibacterial activity, as well as free radical scavenging to assist damaged cells in the healing process. Examples of the need for this are for very large or deep wounds, where a light therapy may be applied to speed the recovery process and prevent infection.

The inventor has determined that most bio-safe antimicrobials and antiseptics are oxidizing and not able to switch their response based on the type of cell presented to it. Nanoceria, known as an antioxidant, has had less success as an antimicrobial. This is because the rate of the surface reaction on nanoceria is low compared to the number of species it would need to deactivate in a given time period ((i.e., $10^5$ viral load or $10^8$ colony-forming unit (CFU) of bacteria)). The mCNPs, described herein, allow for quicker electron recovery of the nanoceria so that it can quickly regenerate its surface creation of oxidizing species. When water is present, this reaction can occur rapidly by digestion of the water by mCNPs, described herein, to these oxidizing species. When a healthy cell is present, the local environment ((i.e., potential hydrogen (pH)) switches the behavior of the mCNPs to be free radical scavenging instead.

Definitions

Unless specifically stated or obvious from context, as used herein, the term "about" is understood as within a range of normal tolerance in the art, for example within 2 standard deviations of the mean. "About" can be understood as within 30%, 25%, 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term "about."

As used herein, the term "epithelial tissue" may include any epithelial tissue including, without limitation, skin, corneal epithelium or the like.

As used herein, the term "composition" or "composite" refers to a product that includes ingredients such as one or more of chemical elements, excipient, diluent, binder, tissue glue, tissue adhesive, surgical glue, an epithelial tissue healing agent, skin healing agent, pharmaceutically acceptable carrier, pharmaceutical agent, or constituent in specified amounts, in addition to any product which results, whether directly or indirectly, from a combination of the ingredients in the specified amounts.

The term "pharmaceutically acceptable" component, as used herein, refers to an ingredient that is suitable for use with humans and/or animals without undue adverse side effects (such as toxicity, irritation, and allergic response) commensurate with a reasonable benefit/risk ratio.

A "pharmaceutically acceptable composition" may contain a pharmaceutically acceptable carrier for delivery or administration of the epithelial tissue healing agent or wound healing composition. The pharmaceutical acceptable compositions may be in the form of solid, semi-solid or liquid dosage forms such as, for example, ointments, liquids, lotions, tablets, powders, pills, capsules, suspensions, or suppositories, or preferably in unit dosage form suitable for single administration of a precise dosage. The pharmaceutically acceptable compositions may include an effective amount of a selected ingredient in combination with a pharmaceutically acceptable carrier and, in addition, may include other pharmaceutical agents such as anti-viral agents, adjuvants, diluents, buffers, and the like. The ingredient may be administered in dosage formulations containing non-toxic pharmaceutically acceptable carriers, adjuvants and vehicles.

The term "wound," as used herein, refers to chronic wound, skin tissue wound, eye wound, sunburn, surgical incisions, lacerations, diabetic ulcer or wound, venous ulcer or wound, corneal ulcer or wound, retinopathy ulcer or wound and similar categories of wounds.

The term "prevention" or "preventing" of a disorder, disease or condition, as used herein, refers to, in a statistical sample, a measurable or observable reduction in the occurrence of the disorder, disease or condition in the treated sample set being treated relative to an untreated control sample set, or delays the onset of one or more symptoms of the disorder, disease or condition relative to the untreated control sample set.

As used herein, the terms "subject," "individual," or "patient" refer to a human, a mammal, or an animal.

The term "therapeutically effective amount," as used herein, refers to an amount of active compound or pharmaceutical agent that elicits the biological or medicinal response in a tissue, system, animal, or human that is being sought by a researcher, veterinarian, medical doctor, or other clinician. A therapeutically effective amount can be given in one or more administrations. The amount of a compound which constitutes a therapeutically effective amount will vary depending on the compound, the disorder and its severity, and the general health, age, sex, body weight and tolerance to drugs of the subject to be treated, but can be determined routinely by one of ordinary skill in the art.

The term "healing," as referred to herein, refers to a process to repair of a wound.

The term "treating" or "treatment," as used herein, covers the treatment of a disorder, disease or condition described herein, in a subject, and includes: (i) inhibiting development of a disorder, disease or condition; (ii) slowing progression of the disorder, disease or condition; (iii) inhibiting, relieving, or slowing progression of one or more symptoms of the disorder, disease or condition; and (iv) assisting with a body's naturally occurring processes heal tissue, such as epithelial tissue, and cause the tissue of a wound to close together.

The term "metal-modified cerium oxide nanoparticles," "metal-modified ceria nanoparticles," or "mCNPs," as used herein, refers to cerium oxide nanoparticles coated with or otherwise bound to an antimicrobial promoting metal such as silver, gold, copper, platinum, nickel, zinc, iron, titanium, ruthenium, vanadium, and the like. The term "mCNPs" includes AgCNP2, as described herein. In an embodiment, the metal-associated cerium oxide nanoparticles comprise a particle size in the range of 3 nm-5 nm or from 1 nm-7 nm.

In some embodiments, the mCNP ingredient with predominately Ce 3+ cerium oxide surface charge may have a particle size in the range of 3 nm-35 nm.

As sometimes used herein, cerium oxide nanoparticles is referred to as "nanoceria."

The inventor has determined that AgCNP1 is catalase mimetic.

The AgCNP1 and AgCNP2 are enzyme mimetic non-stoichiometric nano-cerium oxide. The silver of the synthesis for AgCNP1 and AgCNP2 is a stable metallic silver that is non-ionizing. While not wishing to be bound by theory, the synthesis makes it so that a few atomic layers of the stable metallic silver is anchored into the cerium oxide and contributes to cerium oxide activity (+3 and super oxide dismutase), as opposed to be the direct antimicrobial.

The term "predominant 4+ surface charge" refers to the concentration of cerium ions on the surface and means that the [Ce3+]:[Ce4+] ratio on the surface of the cerium oxide nanoparticle is less than 50%. In a specific example, cerium oxide nanoparticles having a predominant 4+ surface charge have a [Ce3+]:[Ce4+] ratio that is 40% or less. The term "predominant 3+ surface charge" means that the [Ce3+]:[Ce4+] ratio on the surface of the cerium oxide nanoparticle is greater than 50%.

Overview

Diabetes is known to complicate wound healing in many patients and cause ulcers in feet and eyes, for example. Additionally, patients that suffer from circulation issues in their extremities, such as legs, are prone to venous ulcers. These ulcers can become very painful if not treated and lead to more infectious diseases or complications.

Example treatments for wound healing includes a wound healing article or wound healing dressings such as antimicrobial dressings, anti-inflammatory and analgesic dressing and advanced dressings containing biological or naturally derived agents, etc. [See Gwak et al. "Identifying the Trends in Wound-Healing Patents for Successful Investment Strategies," PLOS ONE, Mar. 17, 2017, pages 1-19, DOI: 10.1371/journal.pone.0174203, incorporated herein by reference in full.]

Metal-Modified Cerium Oxide Nanoparticle
(AgCNP2)

Using a forced hydrolysis reaction, a solution containing silver-modified nanoceria and silver secondary phases were formed, hereinafter referred to as "material." The material was washed with distilled water. Then, the washed material was treated with ammonium hydroxide ($NH_4OH$). The material was also treated with a phase transfer complex: mediating aqueous dispersion of dissolved silver, (Ag $[(NH_3)_2OH]_{aq}$). After treatment, the treated material was washed again such as by distilled water. In another synthesis that yields silver modified nanoceria, silver nitrate ($AgNO_3$) and cerium (Ce) are dissolved to form a mixture. Then the mixture is dissolved by hydrogen peroxide ($H_2O_2$) which causes selective oxidation of $Ce^{3+}$ over silver and the evolution of metallic silver phases on the ceria surface. The formula properties for AgCNP2 is shown below in Table 1.

TABLE 1

|  | AgCNP2 | Inorganic Crystal Structure Database No. (ICSD #) |
| --- | --- | --- |
| $Ce^{3+}:Ce^{4+}$ (% $Ce^{3+}$)(%) | 53.7 |  |
| [Ag]/Ag + Ce] by XPS(%) | 4.6 |  |
| SOD Activity (% Inhibition) | 99.2 |  |
| Hydrodynamic Diameter (nm) | 31.6 ± 2.4 |  |
| Zeta Potential (mV) | 24.1 ± 1.3 |  |
| ICPMS Ce concentration (ppb) | 299.2 ± 1.3 |  |
| $E_{corr}$ (mV) | 217.374 |  |
| Metallic Ag |  | 44387 |
| $CeO_2$ |  | 55284 |

A process for metal-mediated nanoscale cerium oxide is described in Craig J. Neal et al., titled "schemMetal-Mediated Nanoscale Cerium Oxide Inactivates Human Coronavirus and Rhinovirus by Surface Disruption," ACS Publications, ACSJCA 8/23/2021, doi.org/10.1021/acsnano.1c04142, incorporated herein by reference in its entirety.

A Zeta-sizer nano was used from Malvern Instruments to determine hydrodynamic diameters and zeta potentials.

Tafel analysis for AgCNP2 shows distinct corrosion potentials. $E_{corr}$ values are substantially more noble than pure silver.

A more detailed description of the process for forming AgCNP2 will now be described. First, about 109 mg of cerium nitrate hexa-hydrate (99.999% purity) is dissolved in about 47.75 mL $dH_2O$ in a 50 ml square glass bottom. Then, about 250 μL of 0.2 M aq. $AgNO_3$ (99% purity) is added to the cerium solution above with the solution vortexed for 2 minutes: Machine: Vortexer. Then, about 2 mL of 3% hydrogen peroxide (stock) is added quickly to the above solution followed by immediate vortexing for 2 minutes at highest rotation speed (in vortexer machine). This solution is stored in dark condition at room temperature with the bottle (50 mL square bottom glass) cap loose to allow for release of evolved gases; solutions are left to age in these conditions for up to 3 weeks (monitoring solution color change from yellow to clear) to create 50 ml total volume of the solution. Particles are then dialyzed against 2 liters of dH2O over 2 days, (dialysis Tubing) with the water changed every 2 hours and stored in the same conditions as for ageing.

The two unique formulations of cerium oxide nanoparticles are produced with surfaces modified by silver nanophases. Materials characterization shows that the silver components in each formulation are unique from each other and decorate the ceria surface as many small nanocrystals (AgCNP1) or as a Janus-type two-phase construct (AgCNP2). The average diameter of AgCNP1 is about 20 to 24 nm, and the average diameter of AgCNP2 is about 3 to 5 nm. However, the inventor prefers the use of AgCNP2, for the reasons stated below.

Each synthesis further possesses unique mixed valency with AgCNP2 possessing a significantly greater fraction of $Ce^{3+}$ states relative to $Ce^{4+}$ over AgCNP1. The distinct valence characters, along with incorporation of chemically active silver phases, lead to high catalytic activities for each formulation. AgCNP2 possesses high superoxide dismutase activity, while AgCNP1 possesses both catalase and superoxide dismutase-like enzyme-mimetic activities, ascribed to the catalase activity of ceria and the superoxide dismutase activity from silver phases.

Further, analysis demonstrates that silver incorporated in each formulation is substantially more stable to redox-mediated degradation than pure silver phases: promoting an increased lifetime in catalytic applications and low probability of ionization of the silver phase.

Although the amount is not intended to be limiting, when used in methods of the invention, some preferred amounts of silver percentages associated with the AgCNPs are about 8% to 15% or less.

In other embodiments, disclosed is a method of producing mCNPs, as described herein, may include the metal of silver. Further, the AgCNP2 is produced via a method comprising dissolving cerium and silver precursor salts such as cerium and silver nitrates; oxidizing the dissolved cerium and silver precursor salts via admixture with peroxide; and precipitating nanoparticles by subjecting the admixture with ammonium hydroxide.

Alternatively, the AgCNPs are produced via a method comprising (i) dissolving cerium and silver precursor salts such as cerium and silver nitrates; (ii) oxidizing and precipitating the dissolved cerium and silver precursor salts via admixture with ammonium hydroxide; (iii) washing and resuspending precipitated nanoparticles in water; (iv) subjecting the resuspended nanoparticles with hydrogen peroxide; and (v) washing the nanoparticles from step (iv) to remove ionized silver.

Applications

The wound healing composition for the epithelial tissue including skin or eye tissue to target the oxidizing response need to kill viruses and bacteria to the virus and bacteria. Additionally, wound healing composition may include an epithelial tissue healing agent and AgCNP2, which acts as an antioxidant in the presence of healthy cells, promoting lower inflammation and cell growth. This allows for quicker closure of the wound while assuring that any trapped bacteria will not lead to an infection. The nature of the wound healing composition is that it works against a broad range of viruses and bacteria.

The epithelial tissue healing agent may be selected from a group consisting of preadipocyte modulator and an adipocyte modulator and contain in a pharmaceutically acceptable composition for subcutaneous administration, as described in U.S. Pat. No. 7,638,484, incorporated herein by reference in its entirety.

The epithelial tissue healing agent may include a therapeutically effective amount of a viral vector comprising a polynucleotide coding for an adipokine, as described in U.S. Pat. No. 7,638,484.

The skin cells colonizing the damaged skin or skin wound may be of any cell type which is involved in the wound healing process, such as keratinocytes, fibroblasts, adipocytes or preadipocytes. The cells can be transformed by a polynucleotide encoding an adipokine as defined hereinbefore. Alternatively, the cells can be transformed by a polynucleotide encoding a polypeptide capable of an adipokine activity, such as the polynucleotide encoding adipsin/complement D activity described in U.S. Pat. No. 5,223,425, incorporated by reference.

The suitable polynucleotide can be introduced into cells by any one of a variety of known methods within the art. Such methods are generally described in Sambrook et al., (1989, 1992), Ausubel et al., (1989), Chang et al., (1995), Vega et al., (1995), Rodriguez and Denhardt (1988) and Gilboa et al., (1986), and include, for example, stable or transient transfection, lipofection, electroporation and infection with recombinant viral vectors. U.S. Pat. No. 4,866,042 discloses a list of vectors involving the central nervous system, and U.S. Pat. No. 5,464,764 and U.S. Pat. No. 5,487,992 describe positive-negative selection methods for inducing homologous recombination, all of which patents are incorporated herein by reference.

The wound healing composition may include a tissue adhesive or glue and metal-modified cerium oxide nanoparticles (mCNPs) in a range of about 3-5 nm in size and mixed in an amount that is in a range of about 0.01 to 0.1 weight percentage of a mixture having the tissue adhesive and the mCNPs.

The tissue adhesive or glue formulation may include the components for delivery and administration to a surgical incision or wound.

In certain embodiments, the tissue glue may include a fibrin glue. Fibrin glue as a surgical adhesive is well known in the art. The tissue glue may include hydrogels comprising, for example, but not limited to, polyethylene glycol (PEG), fibrin, dextrans, including dextrans suitable for chemical crosslinking and/or photo-crosslinking, albumin, polyacrylamide, polyglycolic acid (PGA), polyvinyl chloride, polyvinyl alcohol, poly(n-vinyl-2-pyrollidone), poly(2-hydroxy ethyl methacrylate), hydrophilic polyurethanes, acrylic derivatives, pluronics, such as polypropylene oxide and polyethylene oxide copolymer (POC), or the like.

The use of fibrin glue as a skin adhesive for closing surgical incisions is well known in the art. The glue compositions may also include additional components such as liposomes, for example. Example, fibrin glue compositions are disclosed in U.S. Pat. No. 5,290,552, which is incorporated by reference.

In certain embodiments, the adhesive or glue may comprise non-degradable materials, for example, but not limited to, expanded polytetrafluoroethylene (ePTFE), polytetrafluoroethylene (PTFE), polyethyleneterephthalate (PET), polyurethane, polyethylene, polycabonate, polystyrene, silicone, and the like, or selectively degradable materials, such as poly (lactic-co-glycolic acid; PLGA), polylactic acid (PLA), or PGA.

In certain embodiments, the surgical glue or adhesive may a photo-activated glue, acrylate-based adhesives, and the like.

Example synthetic hydrogels may include polyphosphazenes, poly (vinyl alcohol) (PVA), and an interpenetrating and semi-interpenetrating hydrogels (e.g., PEO, and PEO-PEO-dimethylacrylate blends).

Example tissue adhesives may be a single component adhesive or multi-component adhesive. Further suitable adhesives include synthetic adhesives and/or natural adhesives. Suitable biocompatible adhesives for use in the wound healing composition include commercially available surgical adhesives, such as cyanoacralate (such as 2-octyl cyanoacrylate, Dermabond™) and fibrin glue (such as Tissucol®).

There are many tissue glues, surgical glues, or tissue adhesives readily available on the market. The healing wound composition is applied in a therapeutically effective amount to the wound to close the wound. The amount of AgCNP2 is mixed or dissolved in the wound healing composition in an amount that is a therapeutically effective amount with a surgical adhesive or glue.

The wound healing composition may include a solid composition or a liquid composition, by way of non-limiting example. For a solid composition of a pharmaceutically acceptable composition, conventional nontoxic solid carriers include, for example, pharmaceutical grades of mannitol, starch, magnesium stearate, talc, lactose, glucose, sucrose, sodium saccharin, magnesium carbonate, cellulose, and the like. For liquid pharmaceutically acceptable compositions, the pharmaceutically acceptable composition may be prepared by dissolving, dispersing, mixing, etc., an active compound, as described herein, and optional pharmaceutical adjuvants in an excipient such as, for example, saline, water, aqueous dextrose, ethanol, glycerol, and the like, to thereby form a solution or suspension. The pharmaceutical acceptable composition may contain minor amounts of nontoxic auxiliary substances such as wetting or emulsifying agents, pH buffering agents and the like, for example, sorbitan mono-laurate, sodium acetate, triethanolamine oleate, triethanolamine acetate, etc. Specifically, the wound healing composition includes an amount of AgCNP2 mixed or dissolved in the wound healing composition includes about 0.01 to 0.1 weight percentage (wt %).

Methods of preparing dosage forms of the pharmaceutical acceptable composition are known, or will be apparent, to those skilled in this art. For oral administration, the pharmaceutical acceptable composition will generally take the form of a tablet or capsule, or may be an aqueous or nonaqueous solution, suspension, or syrup. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation of the pharmaceutical acceptable composition herein include, but are not limited to, preservatives, suspending agents, thickening agents, and the like. One skilled in this art may further formulate the pharmaceutical acceptable composition in an appropriate manner, and in accordance with accepted practices, such as those disclosed in Remington's Pharmaceutical Sciences, Gennaro, Ed., Mack Publishing Co., Easton, Pa. 1990.

In some embodiments, multiple applications of a wound healing composition may be needed.

Two tests were performed by MB Research Laboratories, in Spinnerstown, PA, using the AgCNP2 described herein. The tests include a skin irritation test (SIT) and an eye irritation test (EIT).

Skin Irritation Test (SIT) and Results

MatTek EpiDerm™ tissue samples were treated with the test articles, negative control, and positive control in triplicate for 60 minutes. Following treatment and subsequent incubation time, the viability of the tissues was determined using thiazolyl blue tetrazolium bromide (MTT) uptake and reduction. The absorbance of each sample was measured at 570 nm. The viability was then expressed as a percent of control values. If the mean tissue viability was 50% or less, the test material was classified as an irritant; if the mean tissue viability was more than 50%, the test material was classified as a non-irritant. The test used MB Protocol Number: 713-03.

Table 2 below identifies the test and control articles, the mean tissue viability percentage (%), the irritancy classification and the GHS classification. The purpose of this study was to provide classification of the dermal irritation potential of chemicals by using a three-dimensional human epidermis model, according to the OECD Guideline for the Testing of Chemicals No. 439, "In Vitro Skin Irritation: Reconstructed Human Epidermis Test Method". [OECD: Organisation for Economic Co-Operation and Development.] The EpiDerm™ SIT allows discrimination between irritants (Category 2) and non-irritants, in accordance with U.N. GHS classification. [U.N. GHS: United Nations Globally Harmonized System of Classification and Labelling of Chemicals.]

TABLE 2

| Test and Control Article Identity | Mean Tissue Viability (%) | Irritancy Classification | GHS Classification |
|---|---|---|---|
| 0.073 wt % AgCNP2 in water | 112.4 | Non-irritant | No Category |
| 0.01 wt % AgCNP2 in water | 105.8 | Non-irritant | No Category |
| Dulbecco's Phosphate-buffered saline (dPBS) (Negative Control) | 100.0 | Non-irritant | No Category |
| 5% Sodium dodecyl sulfate (Positive Control) | 3.1 | Irritant | Category 2 |

Table 3 shows a table of positive controls.

TABLE 3

| Positive Control | |
|---|---|
| Identity | 5% Sodium dodecyl sulfate (SDS), Lot No. 111120BBB |
| Test Article Characterization | |
| Description | Clear colorless liquid |
| Sample Preparation | Used as received |

Table 4 shows a table of negative controls.

TABLE 4

| Negative Control | |
|---|---|
| Identity | Dulbecco's Phosphate-buffered saline (dPBS) Lot No. 2306404 |
| Test Article Characterization | |
| Description | Clear colorless liquid |
| Sample Preparation | Used as received |

Plate Reader Linearity Check

The linearity of the plate reader used for optical density (OD) determination was verified prior to its use the same week the SIT assay was performed. A dilution series of trypan blue was prepared and two 200-μl aliquots per concentration were pipetted into a 96-well plate. The optical density of the plate wells was measured at a wavelength of 570 nm (OD570), with no reference wavelength. A regression line and an R-squared value were generated using Microsoft Excel® 2007. Verification was considered acceptable if the R-squared value was greater than or equal to 0.999.

Test Article Reduction of MTT

For each test article, a total of 50 μl of the test article were mixed with 1 ml of MTT solution (1 mg/ml methyl thiazole tetrazolium diluted in Dulbecco's Modified Eagle's Medium [DMEM]). A negative control (50 μl of tissue culture water, TCH2O) was tested concurrently. The solutions were incubated in the dark at 37±1° C., 5±1% CO2 for approximately 3 hours in a six-well plate. After incubation, the solutions were visually inspected for purple coloration, which indicates that the test article reduced MTT. Since tissue viability is based on MTT reduction, direct reduction by a test article can exaggerate viability, making a test article seem less irritating than its actual irritation potential. None of the test articles were found to have reduced MTT and the assay continued as per the protocol.

Mesh Compatibility

For each test article, pre-cut nylon mesh supplied with the tissues was placed on a slide and 30 μl of the undiluted test article or tissue culture water (negative control) were applied. After 60 minutes of exposure, the mesh was checked microscopically. No interaction between any test articles or tissue culture water and the mesh was observed so the test articles were dosed using the mesh as a spreading aid.

Assessment of Coloring or Staining Materials

The test articles were non-colored; therefore, it was assessed to determine if the extractant would become colored when mixed with the test article. For each test article, a total of 50 μl of the test article were incubated in a six-well plate with 1 ml of TCH2O for at least one hour in a humidified 37±1° C., 5±1% CO2 incubator. An additional 50 μl of the test article were added to 2 ml of extractant (isopropanol) and incubated for 2 to 3 hours in a six-well plate, at room temperature with shaking. Two 200-μl aliquots of the test article plus TCH2O or test article plus extractant from each well were transferred to a 96-well plate and measured at 570 nm using a plate reader (μQuant Plate Reader, Bio-Tek Instruments, Winooski, VT). No color developed in the water or the extractant, resulting in an OD570 no more than 0.08 after subtraction of blank (TCH2O or isopropanol, respectively), so no colorant controls were added to the assay.

EpiDerm™ Tissue Samples

EpiDerm™ tissues, Lot No. 35611, Kit F, were received from MatTek Corporation (Ashland, MA) on 7 Jul. 2021 and refrigerated at 2 to 8° C. Before use, the tissues were incubated (37±1° C., 5±1% CO2) with assay medium (Mat-Tek) for a one-hour equilibration. The tissues were then moved to new wells with fresh medium for an additional overnight equilibrium, for 18±3 hours. Equilibration medium was replaced with fresh medium before dosing.

Dosing

Each treatment with the test articles or controls was conducted in triplicate. For each test article, 30 μl of the test article were applied to each EpiDerm™ tissue. A nylon mesh was then placed on top to facilitate even distribution of the test article.

A negative control (30 μl of Dulbecco's Phosphate-buffered saline) and a positive control (30 μl of 5% SDS solution) were each tested concurrently, with a nylon mesh placed on top to facilitate even distribution of the material. The exposure period for the test articles and controls was 60 minutes. The dosed tissues were placed in an incubator at 37±1° C., 5±1% CO2 for 35±1 minute, and then returned to the sterile hood for the remainder of the 60-minute exposure period.

After dosing and incubation, the tissues were rinsed with DPBS, blotted to remove the test substance and dry the tissue, and transferred to fresh medium. The rinsed Epi-Derm™ tissues were returned to the incubator for 24±2 hours. Medium was changed at 24±2 hours. Tissues were returned to the incubator for an additional 18±2 hours.

Tissue Viability (MTT Reduction)

Each EpiDerm™ tissue was transferred to a 24-well plate containing 300 μl of MTT solution (1 mg/ml MTT in DMEM). The tissues were then returned to the incubator for an MTT incubation period of 3 hours±10 minutes. Following the MTT incubation period, each EpiDerm™ tissue was rinsed with DPBS and then treated with 2.0 ml of extractant solution (isopropanol) per well for at least two hours, with shaking, at room temperature. Two 200-μl aliquots of the extracted MTT formazan were transferred to a 96-well plate and measured at 570 nm using a plate reader (μQuant Plate Reader, Bio-Tek Instruments, Winooski, VT).

Quality Controls

The assay met the acceptance criteria if the mean OD570 of the negative control tissues was between and 2.8, inclusive, and the mean viability of positive control tissues, expressed as percentage of the negative control tissues, was less than or equal to 20%. In addition, the difference calculated from individual percent tissue viabilities of the three identically-treated replicates was acceptable if it was less than 18%.

Skin Irritation Prediction

According to the EU and GHS classification, an irritant is predicted if the mean relative tissue viability of three individual tissues exposed to the test substance is 50% or less of the mean viability of the negative controls. [EU: OECD Guideline for the Testing of Chemicals No. 439: In Vitro Skin Irritation: Reconstructed Human Epidermis Test Method; and European Centre for the Validation of Alternative Methods (ECVAM) Joint Research Centre (ESAC), Statement on the Scientific Validity of In-Vitro Tests for Skin Irritation Testing.] [GHS: Globally Harmonized System of Classification and Labeling of Chemicals (GHS), 8th revised edition, 2019. United Nations—New York and Geneva.]

Table 5 identifies the irritancy classification and GHS category.

TABLE 5

| In Vitro Result | In Vivo Prediction | |
| --- | --- | --- |
| | Irritancy Classification | GHS |
| Mean tissue viability ≤50% | Irritant | Category 2 |
| Mean tissue viability >50% | Non-Irritant | No Category |

Each tissue in this group had individual relative viabilities greater than 50%, making each tissue non-irritating.

Table 6A is part 1 of a live tissue data table. The table identifies the tissue number to raw data test sample Aliq. 1, Aliq. 2, Aliquots, and mean blank. Table 6B is part 2 of the live tissue data table of Table 5 and identifies the corrected data, mean of Aliquots, OD means and differential, and viabilities both mean and standard deviation.

TABLE 6A

| Test and Control Article Identity | Tissue No. | Raw data Aliq. 1 | Aliq. 2 | Mean Blank |
| --- | --- | --- | --- | --- |
| 0.073 wt % AgCNP2 in water | 1 | 1.870 | 2.307 | 0.047 |
| | 2 | 2.189 | 2.154 | |
| | 3 | 1.722 | 1.698 | |
| 0.01 wt % AgCNP2 in water | 1 | 1.857 | 2.108 | 0.047 |
| | 2 | 1.867 | 1.826 | |
| | 3 | 1.789 | 1.806 | |
| Dulbecco's Phosphate-buffered saline (dPBS) (Negative Control) | 1 | 1.861 | 1.752 | 0.047 |
| | 2 | 1.600 | 1.652 | |
| | 3 | 1.939 | 1.850 | |
| 5% Sodium dodecyl sulfate (SDS) (Positive Control) | 1 | 0.091 | 0.112 | 0.047 |

TABLE 6B

| Test and Control | Tissue | Corrected Data | | Mean of | % | OD | | Viabilities (%) | |
|---|---|---|---|---|---|---|---|---|---|
| Article Identity | No. | Aliq. 1 | Aliq. 2 | Aliquots | Viability | Mean | Diff. | Mean | SD |
| 0.073 wt % AgCNP2 | 1 | 1.823 | 2.260 | 2.042 | 118.1 | 1.943 | 0.246 | 112.4 | 14.2 |
| in water | 2 | 2.142 | 2.107 | 2.125 | 122.9 | | | | |
| | 3 | 1.675 | 1.651 | 1.663 | 96.2 | | | | |
| 0.01 wt % AgCNP2 | 1 | 1.810 | 2.061 | 1.936 | 112.0 | 1.829 | 0.096 | 105.8 | 5.5 |
| in water | 2 | 1.820 | 1.779 | 1.800 | 104.1 | | | | |
| | 3 | 1.742 | 1.759 | 1.751 | 101.3 | | | | |
| Dulbecco's Phosphate- | 1 | 1.814 | 1.705 | 1.760 | 101.8 | 1.729 | 0.137 | 100.0 | 7.9 |
| buffered saline (dPBS) | 2 | 1.553 | 1.605 | 1.579 | 91.3 | | | | |
| (Negative Control) | 3 | 1.892 | 1.803 | 1.848 | 106.9 | | | | |
| 5% Sodium dodecyl | 1 | 0.044 | 0.065 | 0.055 | 3.2 | 0.054 | 0.003 | 3.1 | 0.1 |
| sulfate (SDS) | 2 | 0.052 | 0.050 | 0.051 | 3.0 | | | | |
| (Positive Control) | 3 | 0.059 | 0.053 | 0.056 | 3.2 | | | | |

Table 7 identifies the OD blank values.

TABLE 7

| Tissue: | 1 | 2 | 3 | 4 | 5 | 6 | Mean Blank OD |
|---|---|---|---|---|---|---|---|
| OD: | 0.048 | 0.046 | 0.046 | 0.048 | 0.047 | 0.046 | 0.047 |

Quality Controls

The mean OD570 of the negative control tissues was 1.729, which met the acceptance criteria of greater than or equal to 0.8 and less than or equal to 2.8. The mean relative viability of the positive control tissues was 3.1%, which met the acceptance criterion of less than or equal to 20%. The standard deviation in viability between identically treated tissues were 0.1% to 19.6%, which did not meet the acceptance criterion of less than 18%. The R-squared value calculated for the plate reader linearity check was 0.9997, which met the acceptance criterion of greater than or equal to 0.999.

Table 8 identifies the PBS. Dulbeccos W/O CA. MG (1×) with an origin of the UK.

TABLE 8

| Test | Specification | Result | Units |
|---|---|---|---|
| a01 Bacterial | Negative | Negative | |
| a02 Fungal | Negative | Negative | |
| a96 Endotoxin | 0.000 to 0.500 | 0.040 | EU/mL |
| b01 Ph | 7.00 to 7.30 | 7.17 | pH Units |
| b02 Osmolality | 270 to 300 | 283 | mOs/kg H2O |
| b33 Volume | Satisfactory | Satisfactory | |
| q01 Documentation | Satisfactory | Satisfactory | |
| q02 Appearance (Liquid) | Satisfactory | Satisfactory | |
| Sterile filtered (0.1 μm); | | | |
| Sterility testing (Test | | | |
| Numbers a01, a02) is | | | |
| carried out in accordance | | | |
| with *Ph. Eur. 2.6.1* and | | | |
| *USP 7.1* | | | |

Eye Irritation Test (EIT) and Results

MatTek EpiOcular™ tissues were treated with the test articles, negative control, and positive control in duplicate for 30 minutes. Following treatment and subsequent incubation time, the viability of the tissues was determined using thiazolyl blue tetrazolium bromide (MTT) uptake and reduction. The absorbance of each sample was measured at 570 nm. The viability was then expressed as a percent of negative control values. If the mean tissue viability were less than or equal to 60%, the test material was classified as an Irritant (UN GHS Category 1 or 2); if the mean tissue viability were greater than 60%, the test material was classified as UN GHS No Category, and was therefore interpreted to be Non-irritant. The MB protocol: 772.

Table 9 shows the irritancy classification and GHS classification, as well as the tissue viability for mean and difference for each test article.

The summarized results and irritation classifications are as follows, as shown in Table 9:

TABLE 9

| Test and Control | Tissue Viability (%) | | Irritancy Classifi- | GHS Classifi- |
|---|---|---|---|---|
| Article Identity | Mean | Diff. | cation | cation |
| Test Article 1: 0.073 wt % AgCNP2 in water | 96.8 | 13.47 | Non-Irritant | No Category |
| Test Article 2: 0.01 wt % AgCNP2 in water | 105.2 | 4.61 | Non-Irritant | No Category |
| Tissue Culture Water (Run 1) (Negative Control) | 100.0 | 2.51 | Non-Irritant | No Category |
| Methyl acetate (Run 1) (Positive Control) | 30.1 | 4.28 | Irritant | Category 1 or 2 |
| Tissue Culture Water (Run 2) (Negative Control) | 100.0 | 5.63 | Non-Irritant | No Category |
| Methyl acetate (Run 2) (Positive Control) | 40.9 | 1.28 | Irritant | Category 1 or 2 |
| Diff. = difference between tissues | | | | |

The purpose of this study was to provide classification of chemicals concerning their eye irritation potential using an alternative to the Draize Rabbit Eye Test, according to the OECD Test Guideline No. 492, "Reconstructed Human Cornea-like Epithelium (RhCE) Test Method for Identifying Chemicals Not Requiring Classification and Labelling for Eye Irritation or Serious Eye Damage." The EpiOcular™ EIT was intended to differentiate those materials that are UN GHS No Category (i.e., do not meet the requirements for UN GHS classification) from those that would require labeling as either UN GHS Category 1 or 2.

Limitation

This assay was not intended to differentiate between UN GHS Category 1 and UN GHS Category 2 (nor between EU R36 and R41).

Table 10 lists a description of the test articles.

TABLE 10

| Identity | Description | Sample Preparation |
|---|---|---|
| Test Article 1: 0.073 wt % AgCNP2 in water | Clear Colorless Liquid | Used as received |
| Test Article 2: 0.01 wt % AgCNP2 in water | Clear Colorless Liquid | Used as received |

Table 11 lists a description of the Positive control and Table 12 lists a description of the Negative Control.

TABLE 11

| Positive Control | |
|---|---|
| Identity | Methyl acetate, Lot No. 060321JKA (Characterization not provided by supplier) |
| Storage | Room temperature and humidity |
| Description | Clear colorless |
| Provided by | MatTek Corporation |

TABLE 12

| Negative Control | |
|---|---|
| Identity | Tissue Culture Water, (TCH2O) Lot No. RNBJ0203 |
| Storage | Room temperature and humidity |
| Description | Clear colorless |
| Provided by | Sigma-Aldrich ® |

Plate Reader Linearity Check

The linearity of the plate reader used for optical density (OD) determination was verified prior to its use the same week the EIT assay was performed. A dilution series of trypan blue was prepared and two 200-µl aliquots per concentration were pipetted into a 96-well plate. The optical density of the plate wells was measured at a wavelength of 570 nm (OD570), with no reference wavelength. A regression line and an R-squared value were generated using Microsoft Excel® 2007. Verification was considered acceptable if the R-squared value was greater than 0.999.

Test Article Reduction of MTT

For each test article, A total of 50 µl of the test article were mixed with 1 ml of MTT solution (1 mg/ml methyl thiazole tetrazolium diluted in Dulbecco's Modified Eagle's Medium [DMEM]). A negative control (50 µl of tissue culture water, TCH2O) was tested concurrently. The solutions were incubated in the dark at 37±1° C., 5±1% CO2 for approximately 3 hours in a six-well plate. After incubation, the solutions were visually inspected for purple coloration, which indicates that the test article reduced MTT. Since tissue viability is based on MTT reduction, direct reduction by a test article can exaggerate viability, making a test article seem less irritating than its actual irritation potential. None of the test articles were found to have reduced MTT and the assay continued as per the protocol.

Assessment of Coloring or Staining Materials

The test articles 0.073 wt % AgCNP2 in water and 0.01 wt % AgCNP2 in water, were non-colored; therefore, they were assessed to determine if the extractant would become colored when mixed with the test article.

For each test article, a total of 50 µl of the test article were incubated in a six-well plate with 1 ml of TCH2O for at least one hour in a humidified 37±1° C., 5±1% CO2 incubator. An additional 50 µl of the test article were added to 2 ml of extractant (isopropanol) and incubated for 2 to 3 hours in a six-well plate, at room temperature with shaking. Two 200-µl aliquots of the test article plus TCH2O or test article plus extractant from each well were transferred to a 96-well plate and measured at 570 nm using a plate reader (µQuant Plate Reader, Bio-Tek Instruments, Winooski, VT). No color developed in the water or the extractant, resulting in an OD570 no more than 0.08 after subtraction of blank (TCH2O or isopropanol, respectively), so no colorant controls were added to the assay.

EpiOcular™ Tissue Samples

EpiOcular™ tissues, Lot No. 31794, Kit C and A, were received from MatTek Corporation (Ashland, MA) on Jun. 29, 2021, and refrigerated at 2 to 8° C. Before use, the tissues were incubated (37±1° C., 5±1% CO2) with assay medium (MatTek) for a one-hour equilibration. Equilibration medium was replaced with fresh medium for an additional overnight equilibration of 16 to 24 hours. After the overnight incubation, the tissues were moistened with 20 µl of Dulbecco's phosphate-buffered saline (DPBS) and incubated at 37±1° C., 5±1% CO2 for 30±2 minutes.

Dosing

For each test article, a total of 50 µl of the test article were applied to EpiOcular™ tissues. A negative control (50 µl of TCH2O) and a positive control (50 µl of methyl acetate) were each tested concurrently. Each treatment with test article or control was conducted in duplicate. The tissues were incubated at 37±1° C., 5±1% CO2 for 30±2 minutes. After dosing and incubation, the tissues were rinsed with PBS and soaked in 5 ml of room-temperature assay medium in a 12-well plate for 12±2 minutes. The soaked tissues were then incubated in fresh assay medium at 37±1° C., 5±1% CO2 for 120±15 minutes.

Tissue Viability (MTT Reduction)

At the end of the incubation period, each EpiOcular™ tissue was transferred to a 24-well plate containing 300 µl of MTT solution (1 mg/ml MTT in DMEM). The tissues were then returned to the incubator for an MTT incubation period of 3 hours±10 minutes. Following the MTT incubation period, each EpiOcular™ tissue was rinsed with DPBS and then treated with 2.0 ml of extractant (isopropanol) in a 24-well plate overnight at room temperature in the dark allowing extraction to occur through both the top and bottom of the insert. Two 200-µl aliquots of the extracted MTT formazan from each well were transferred to a 96-well plate and measured at 570 nm using a plate reader (µQuant Plate Reader, Bio-Tek Instruments, Winooski, VT).

Analysis of Data

Viability:

See Tables 13A and 13B for Experimental Data. The mean absorbance value for each time point was calculated from the optical density (OD) of the duplicate samples and expressed as percent viability for each sample using the following formula Eq(1):

$$\% \text{ viability}=100\times(OD\text{sample}/OD\text{negative control}) \quad Eq(1)$$

Quality Controls

The assay meets the acceptance criteria if the mean OD570 of the negative control tissues is greater than 0.8 and less than 2.5, and the mean relative viability of positive control tissues, expressed as percentage of the negative control tissues, is less than 50%. In addition, the difference in viability between identically treated tissues must be less than 20%.

Ocular Irritation Prediction

According to the OECD Guideline, and GHS classification, an irritant is predicted if the mean relative tissue viability of two individual tissues exposed to the test substance is <60% of the mean viability of the negative controls. Table 13 shows the mean tissue viability for the GHS Classification.

TABLE 13

| In Vitro Result | GHS Classification |
|---|---|
| Mean tissue viability less than or equal to 60% | Category 1 or 2 |
| Mean tissue viability greater than 60% | No Category |

If the test article-treated tissue viability is 60±5%, a second EIT should be performed. If the results of the second test disagree with the first, then a third test should be performed. The conclusion will be based on the agreement of two of the three tests.

Tables 14A and 14B show the experimental data, per test article. Table 14A shows the raw OD, the blank corrected OD data and mean of aliquots. Table 14B shows the percent viability per test article, the OD mean, OD difference, the viability % means and the viability % difference. Table 15A shows the OD blank data for run 1. Table 15B shows the OD blank data for run 2.

TABLE 14A

| Test and Control Article Identity | Tissue No. | Raw OD data Aliq. 1 | Aliq. 2 | Blank corrected OD data Aliq. 1 | Aliq. 2 | Mean of Aliquots |
|---|---|---|---|---|---|---|
| Test Article 1: 0.073 wt % | 1 | 2.096 | 2.330 | 2.049 | 2.283 | 2.166 |
| AgCNP2 in water (Run 1) | 2 | 1.822 | 2.040 | 1.775 | 1.993 | 1.884 |
| Test Article 2: 0.01 wt % | 1 | 2.179 | 2.220 | 2.132 | 2.173 | 2.153 |
| AgCNP2 in water (Run 1) | 2 | 2.324 | 2.268 | 2.277 | 2.221 | 2.249 |
| TCH2O (Run 1) | 1 | 2.092 | 2.240 | 2.045 | 2.193 | 2.119 |
| (Negative Control) | 2 | 2.097 | 2.130 | 2.050 | 2.083 | 2.067 |
| Methyl acetate (Run 1) | 1 | 0.636 | 0.628 | 0.589 | 0.581 | 0.585 |
| (Positive Control) | 2 | 0.710 | 0.733 | 0.663 | 0.686 | 0.675 |
| TCH2O (Run 2) | 1 | 2.354 | 2.141 | 2.308 | 2.095 | 2.201 |
| (Negative Control) | 2 | 2.166 | 2.088 | 2.120 | 2.042 | 2.081 |
| Methyl acetate (Run 2) | 1 | 0.934 | 0.939 | 0.888 | 0.893 | 0.890 |
| (Positive Control) | 2 | 0.911 | 0.907 | 0.865 | 0.861 | 0.863 |

TABLE 14B

| Test and Control Article Identity | Tissue No. | % Viability | OD Mean | Diff. | % Viabilities Mean | Diff. |
|---|---|---|---|---|---|---|
| Test Article 1: 0.073 wt % | 1 | 103.5 | 2.025 | 0.282 | 96.8 | 13.47 |
| AgCNP2 in water (Run 1) | 2 | 90.0 | | | | |
| Test Article 2: 0.01 wt % | 1 | 102.9 | 2.201 | 0.096 | 105.2 | 4.61 |
| AgCNP2 in water (Run 1) | 2 | 107.5 | | | | |
| | 2 | 9.4 | | | | |
| TCH2O (Run 1) | 1 | 101.3 | 2.093 | 0.053 | 100.0 | 2.51 |
| (Negative Control) | 2 | 98.7 | | | | |
| Methyl acetate (Run 1) | 1 | 28.0 | 0.630 | 0.089 | 30.1 | 4.28 |
| (Positive Control) | 2 | 32.2 | | | | |
| TCH2O (Run 2) | 1 | 102.8 | 2.141 | 0.121 | 100.0 | 5.63 |
| (Negative Control) | 2 | 97.2 | | | | |
| Methyl acetate (Run 2) | 1 | 41.6 | 0.877 | 0.028 | 40.9 | 1.28 |
| (Positive Control) | 2 | 40.3 | | | | |

Diff. = difference between tissues

OD = optical density

TABLE 15A

| | | | | Blank Data Run 1: | | | | | |
|---|---|---|---|---|---|---|---|---|---|
| No. | 1 | 2 | 3 | 4 | 5 | 6 | 7 | 8 | Mean |
| OD | 0.47 | 0.47 | 0.46 | 0.46 | 0.46 | 0.47 | 0.46 | 0.48 | 0.47 |

TABLE 15B

| | | | | Run 2: | | | | | |
|---|---|---|---|---|---|---|---|---|---|
| No. | 1 | 2 | 3 | 4 | 5 | 6 | 7 | 8 | Mean |
| OD | 0.46 | 0.46 | 0.46 | 0.46 | 0.46 | 0.46 | 0.46 | 0.47 | 0.46 |

Quality Controls

The mean OD570 of the negative control tissues were 2.093 and 2.141, which met the acceptance criteria of greater than 0.8 and less than 2.5. The mean relative viabilities of the positive control tissues were 30.1% and 40.9%, which met the acceptance criterion of less than 50%. The differences in viability between identically treated tissues were 1.03% to 13.47%, which met the acceptance criterion of less than 20%. The R-squared value calculated for the plate reader linearity check was 0.9999, which met the acceptance criterion of greater than 0.999. All controls passed the acceptance criteria for a valid study.

Treatment/Prevention

Epithelial Tissue Wound Healing

In view of the foregoing, the embodiments herein are directed to a wound healing composition comprising metal-modified cerium oxide nanoparticles (mCNPs), as described herein, having a predominant 3+ surface charge and a tissue glue, tissue adhesive, or surgical glue, the metal-modified cerium oxide nanoparticles (mCNPs) is in an amount ranging from about 0.01-0.1% by weight and the metal is non-ionizing with antimicrobial promoting properties.

In some embodiments, the wound healing composition comprising metal-modified cerium oxide nanoparticles (mCNPs), as described herein, and a tissue glue, tissue adhesive, or surgical glue, the mCNPs to oxidize viruses and bacteria, which cause infections, but also in the presence of a healthy human cell, change its behavior to anti-oxidizing.

In some embodiments, the wound healing composition comprising metal-modified cerium oxide nanoparticles (mCNPs), as described herein, and an epithelial tissue healing agent, the mCNPs to oxidize viruses and bacteria, which cause infections, but also in the presence of a healthy human cell, change its behavior to anti-oxidizing, the mCNPs having a predominant 3+ surface charge and in an amount from about 0.01-0.1% by weight of a mixture of the epithelial tissue healing agent and the mCNPs.

The wound healing composition may include a metal selected from the group consisting of silver, gold, ruthenium, vanadium, copper, titanium, nickel, platinum, titanium, tin, zinc and iron. The metal is a stable metallic metal. The metal is a non-ionic metal with antimicrobial promoting properties.

In some embodiments, the wound healing composition comprises AgCNP2 having a predominant 3+ surface charge and in an amount of less than about 0.01 to 0.1% by weight in the wound healing composition.

The mCNPs of the wound healing composition are in the range of about 3-5 nm in size. In some embodiments, the mCNP ingredient with predominately Ce 3+ cerium oxide surface charge may have a particle size in the range of 3 nm-35 nm.

The mCNPs of the wound healing composition may comprise a predominantly 3+ cerium atom charge and a non-ionizing metal with antimicrobial properties.

The pharmaceutical acceptable composition may include an epithelial tissue healing agent selected from a group consisting of preadipocyte modulator and an adipocyte modulator and contain in a pharmaceutically acceptable composition for subcutaneous administration, and AgCNP2 having a predominant 3+ surface charge and in an amount of about 0.01 to 0.1% by weight of a mixture of the epithelial tissue healing agent and the AgCNP2.

The pharmaceutical acceptable composition may include an epithelial tissue healing agent selected from a group consisting of preadipocyte modulator and an adipocyte modulator and contain in a pharmaceutically acceptable composition for ocular tissue administration, and AgCNP2 having a predominant 3+ surface charge and in an amount of about 0.01 to 0.1% by weight.

The pharmaceutical acceptable composition may include an epithelial tissue healing agent in a pharmaceutically acceptable carrier for ocular tissue administration, and mCNPs or AgCNP2 in an amount of about 0.01 to 0.1% by weight of the epithelial tissue healing agent. The metal-modified cerium oxide nanoparticles (mCNPs) have a predominant 3+ surface charge and in a range of about 3-5 nm or 3-35 nm in size and mixed in an amount that is in a range of about 0.01 to 0.1 weight percentage of a mixture having the epithelial tissue healing agent and the mCNPs. The metal may be a non-ionizing antimicrobial promoting metal.

The pharmaceutical acceptable composition may include an epithelial tissue healing agent containing a polynucleotide in a pharmaceutically acceptable carrier for skin tissue administration, and AgCNP2 having a predominant 3+ surface charge and in an amount of about 0.01 to 0.1% by weight of the epithelial tissue healing agent. The silver is a stable metallic silver that is non-ionizing.

The pharmaceutical acceptable composition may include an epithelial tissue healing agent containing a polynucleotide in a pharmaceutically acceptable carrier for epithelial tissue administration, and AgCNP2 having a predominant 3+ surface charge and in an amount of about 0.01 to 0.1% by weight of a mixture including the epithelial tissue healing agent and the AgCNP2. The silver is a stable metallic silver that is non-ionizing.

Moreover, the method may include treating wounds with the mCNPs, described herein, and/or a wound healing composition including the mCNPs in an amount of less than about 0.01 to 0.1% by weight in the wound healing composition to assist with a body's naturally occurring processes to oxidize viruses and bacteria, which cause infections, but also in the presence of a healthy human cell, change its behavior to anti-oxidizing where the mCNPs in the wound healing composition have a predominant 3+ surface charge and are in the range of about 3-5 nm or 3-35 nm in size. The metal (m) is a non-ionizing stable metallic metal.

Moreover, the method may include treating epithelial tissue with the mCNPs, described herein, and/or a pharmaceutically acceptable composition including an epithelial tissue healing agent and the mCNPs in an amount of less than about 0.01 to 0.1% by weight in the pharmaceutically acceptable composition to assist with a body's naturally occurring processes to oxidize viruses and bacteria, which cause infections, but also in the presence of a healthy human cell, change its behavior to anti-oxidizing where the mCNPs in the wound healing composition have a predominant 3+ surface charge and are in the range of about 3-5 nm or 3-35 nm in size. The metal (m) is a non-ionizing stable metallic metal.

In some embodiments, the AgCNP2 of the wound healing composition or pharmaceutically acceptable composition for the treatment of epithelial tissue is produced via a method comprising dissolving cerium and silver precursor salts such as cerium and silver nitrates and oxidizing the dissolved cerium and silver precursor salts.

In some embodiments, the AgCNP2 of the wound healing composition or pharmaceutically acceptable composition for the treatment of epithelial tissue is produced via a method comprising dissolving cerium and silver precursor salts such as cerium and silver nitrates; oxidizing the dissolved cerium and silver precursor salts via admixture with peroxide; and precipitating nanoparticles by subjecting the admixture with ammonium hydroxide.

In some embodiments, the AgCNP2 of the wound healing composition or pharmaceutically acceptable composition is produced via a method comprising (i) dissolving cerium and silver precursor salts such as cerium and silver nitrates; (ii) oxidizing and precipitating the dissolved cerium and silver precursor salts via admixture with ammonium hydroxide; (iii) washing and resuspending precipitated nanoparticles in water; (iv) subjecting the resuspended nanoparticles with hydrogen peroxide; and (v) washing the nanoparticles from step (iv) to remove ionized silver where the mCNPs in the wound healing composition have a predominant 3+ surface charge and are in the range of about 3-5 nm or 3-35 nm in size.

In some embodiments, the AgCNP2 of the pharmaceutically acceptable composition is produced via a method comprising (i) dissolving cerium and silver precursor salts such as cerium and silver nitrates; (ii) oxidizing and precipitating the dissolved cerium and silver precursor salts via admixture with ammonium hydroxide; (iii) washing and resuspending precipitated nanoparticles in water; (iv) subjecting the resuspended nanoparticles with hydrogen peroxide; and (v) washing the nanoparticles from step (iv) to remove ionized silver where the mCNPs in the wound healing composition have a predominant 3+ surface charge and are in the range of about 3-5 nm or 3-35 nm in size.

In some embodiments, a method is provided of inducing or accelerating a healing process of a damaged skin or skin wound, by administering to the skin cells colonizing the damaged skin or skin wound area a therapeutically effective amount of a wound healing composition including AgCNP2 and a viral vector comprising a polynucleotide coding for an adipokine, thus transforming said skin cells to express and secrete said adipokine, thereby inducing or accelerating the healing process of the damaged skin or skin wound, where the AgCNP2 has a predominant 3+ surface charge and a size in the range of about 3-5 nm or 3-25 nm and in an amount of 0.01 to 0.1 wt. % of the wound healing composite to assist with a body's naturally occurring processes to oxidize viruses and bacteria, which cause infections, but also in the presence of a healthy human cell, change its behavior to anti-oxidizing. The silver (Ag) is a stable metallic silver that is non-ionizing.

In some embodiments, a wound healing composition includes a viral vector comprising polynucleotide coding for an adipokine, to transform skin cells to express and secrete adipokine and AgCNP2 having a predominant 3+ surface charge and a size in the range of about 3-5 nm or 3-35 nm and in an amount of 0.01 to 0.1 wt. % of the wound healing composite to assist with a body's naturally occurring processes to oxidize viruses and bacteria, which cause infections, but also in the presence of a healthy human cell, change its behavior to anti-oxidizing.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising." Moreover, unless specifically stated, any use of the terms first, second, etc., does not denote any order or importance, but rather the terms first, second, etc., are used to distinguish one element from another. As used herein the expression "at least one of A and B," will be understood to mean only A, only B, or both A and B.

While various disclosed embodiments have been described above, it should be understood that they have been presented by way of example only, and not limitation. Numerous changes, omissions and/or additions to the subject matter disclosed herein can be made in accordance with the embodiments disclosed herein without departing from the spirit or scope of the embodiments. Also, equivalents may be substituted for elements thereof without departing from the spirit and scope of the embodiments. In addition, while a particular feature may have been disclosed with respect to only one of several implementations, such feature may be combined with one or more other features of the other implementations as may be desired and advantageous for any given or particular application. Furthermore, many modifications may be made to adapt a particular situation or material to the teachings of the embodiments without departing from the scope thereof.

Therefore, the breadth and scope of the subject matter provided herein should not be limited by any of the above explicitly described embodiments. Rather, the scope of the embodiments should be defined in accordance with the following claims and their equivalents.

What is claimed is:

1. A wound healing composition comprising:
a tissue adhesive; and
silver-modified cerium oxide nanoparticles (AgCNPs) consisting of a predominant Ce3+ surface charge mixed in an amount that is in a range of about 0.01 to 0.1 weight percentage of a mixture having the tissue adhesive and the AgCNPs wherein the AgCNPs include stable metallic silver (Ag) that is non-ionizing, a Janus-type two-phase construct and an antimicrobial promoting metal wherein about is at least one of 30%, 25%, 20%, 15%, 10%, 9%, 8%, 7%, 6%, 5%, 4%, 3%, 2%, 1%, 0.5%, 0.1%, 0.05%, or 0.01% of the range.

2. The wound healing composition according to claim 1, wherein the tissue adhesive is a therapeutically effective amount of a surgical adhesive.

3. The wound healing composition according to claim 1, wherein the tissue adhesive comprises one of cyanoacralate, 2-octyl cyanoacrylate or fibrin glue.

4. The wound healing composition according to claim 1, wherein the tissue adhesive includes a hydrogel consisting of at least one of polyethylene glycol (PEG), fibrin, a dextran suitable for chemical crosslinking, a dextran suitable for photo-crosslinking, albumin or polyacrylamide.

5. The wound healing composition according to claim 1, the adhesive comprises non-degradable materials selected from a group consisting of: expanded polytetrafluoroethylene (ePTFE), polytetrafluoroethylene (PTFE), polyethylene-terephthalate (PET), polyurethane, polyethylene, polycarbonate, polystyrene, silicone, or degradable materials that include one of poly (lactic-co-glycolic acid; PLGA), poly-lactic acid (PLA), or polyglycolic acid (PGA).

6. A wound healing composition comprising:
an epithelial tissue healing agent; and
silver-modified cerium oxide nanoparticles (AgCNPs) consisting of a predominant Ce3+ surface charge mixed in an amount that is in a range of about 0.01 to 0.1 weight percentage of a mixture having the epithelial tissue healing agent and the AgCNPs wherein the AgCNPs include a stable metallic silver (Ag) that is non-ionizing and a Janus-type two-phase construct wherein about is at least one of 30%, 25%, 20%, 15%, 10%, 9%, 8%, 7%, 6%, 5%, 4%, 3%, 2%, 1%, 0.5%, 0.1%, 0.05%, or 0.01% of the range.

7. The wound healing composition according to claim 6, wherein the epithelial tissue healing agent is selected from a group consisting of a preadipocyte modulator and an adipocyte modulator and contains in a pharmaceutically acceptable composition for subcutaneous administration.

8. The wound healing composition according to claim 6, wherein the epithelial tissue healing agent of the mixture contains a polynucleotide in a pharmaceutically acceptable carrier for skin tissue administration.

9. The wound healing composition according to claim 6, wherein the epithelial tissue healing agent of the mixture is selected from a group consisting of preadipocyte modulator and an adipocyte modulator and contains in a pharmaceutically acceptable composition for ocular tissue administration.

10. The wound healing composition according to claim 6, wherein the epithelial tissue healing agent of the mixture contains a pharmaceutically acceptable carrier for ocular tissue administration.

11. The wound healing composition according to claim 6, wherein the epithelial tissue healing agent of the mixture comprises a viral vector comprising polynucleotide coding for an adipokine to transform skin cells to express and secrete adipokine.

12. A method comprising:
treating skin tissue of a wound with a wound healing composition of claim 1.

13. The method according to claim 12, wherein the wound is a surgical incision formed in the skin tissue.

14. A method comprising:
treating epithelial tissue with a wound healing composition of claim 8.

15. The method according to claim 14, wherein the epithelial tissue is ocular tissue.

16. The method according to claim 14, wherein the epithelial tissue is skin cells and the treating includes:
administering to the skin cells colonizing damaged skin or a skin wound area a therapeutically effective amount of the wound healing composition,
wherein the epithelial tissue healing agent of the mixture includes a viral vector comprising a polynucleotide coding for an adipokine.

17. The method according to claim 14, wherein the epithelial tissue is skin cells and the treating includes:
administering to the skin cells colonizing damaged skin or a skin wound area of ocular tissue a therapeutically effective amount of the wound healing composition,
wherein the epithelial tissue healing agent of the mixture is selected from a group consisting of preadipocyte modulator and an adipocyte modulator and contains in a pharmaceutically acceptable composition for the ocular tissue.

18. The method according to claim 12, wherein the epithelial tissue is skin cells of a surgical incision and the treating includes:
administering to the skin cells a therapeutically effective amount of the wound healing composition,
wherein the tissue adhesive of the mixture includes a therapeutically effective amount of a surgical adhesive.

19. The method according to claim 12, wherein the epithelial tissue is skin cells and the treating includes:
administering to the skin cells colonizing damaged skin or a skin wound area a therapeutically effective amount of the wound healing composition,
wherein the tissue adhesive of the mixture includes a hydrogel consisting of at least one of polyethylene glycol (PEG), fibrin, a dextran suitable for chemical crosslinking, a dextran suitable for photo-crosslinking, albumin or polyacrylamide.

20. A wound healing composition consisting of:
a tissue adhesive; and
metal-modified cerium oxide nanoparticles (mCNPs) consisting of a predominant Ce3+ surface charge mixed in an amount that is in a range of about 0.01 to 0.1 weight percentage of a mixture having the tissue adhesive and the mCNPs wherein the m is an antimicrobial promoting metal consisting of one of silver, gold, or platinum wherein about is at least one of 30%, 25%, 20%, 15%, 10%, 9%, 8%, 7%, 6%, 5%, 4%, 3%, 2%, 1%, 0.5%, 0.1%, 0.05%, or 0.01% of the range.

21. The wound healing composition according to claim 1, wherein the predominant Ce3 surface charge is greater than 53.7 percent.

22. The wound healing composition according to claim 6, wherein the predominant Ce3+ surface charge is greater than 53.7 percent.

* * * * *